United States Patent [19]

Engira

[11] Patent Number: 5,339,824
[45] Date of Patent: Aug. 23, 1994

[54] MEMORY LOOP ECG RECORDER WITH LIFO DATA TRANSMISSION

[75] Inventor: Ram M. Engira, Milwaukee, Wis.

[73] Assignee: Cardiac Evaluation Center, Inc., Madison, Wis.

[21] Appl. No.: 957,545

[22] Filed: Oct. 6, 1992

[51] Int. Cl.$^5$ .......................... A61B 5/0432
[52] U.S. Cl. ................... 128/712; 128/904; 128/710
[58] Field of Search ............ 128/712, 696, 702, 705, 128/709, 710, 903, 904

[56] References Cited

U.S. PATENT DOCUMENTS

| | | |
|---|---|---|
| 4,622,979 | 11/1986 | Katchis et al. .................. 128/702 |
| 4,889,134 | 12/1989 | Greenwold et al. .............. 128/696 |
| 5,226,431 | 7/1993 | Bible et al. ................. 128/710 X |

*Primary Examiner*—Lee S. Cohen
*Assistant Examiner*—Jeffrey R. Jastrzab
*Attorney, Agent, or Firm*—Quarles & Brady

[57] ABSTRACT

A memory loop recorder records electrocardiographic data in a random access memory for transmission to a remote display terminal via telephone line. The ECG data in the loops is transmitted in reverse time-order to the display from a point related to the occurrence of symptoms. The remote display terminal displays the transmitted data from right to left thus correcting the time access of the graphical display but allowing more rapid diagnosis of the critical ECG data.

15 Claims, 4 Drawing Sheets

MEMORY LOOP ECG RECORDER WITH LIFO DATA TRANSMISSION

FIELD OF THE INVENTION

This invention relates to electrocardiographs and specifically to portable electrocardiographs capable of transmitting electrocardiographic signals to a remote display terminal.

BACKGROUND OF THE INVENTION

A cornerstone in the diagnosis of heart abnormalities is the electrocardiograph. With a typical electrocardiograph, conductive leads connect electrodes placed on the patient to a stationary measuring machine while the patient rests on a cot or the like.

For episodic abnormalities, the electrocardiogram ("ECG") recorded by the electrocardiograph desirably covers a period of time preceding the episode ("pre-symptom data") and after the episode ("post-symptom data"). Yet immobilizing the patient during the acquisition of such pre-symptom and post-symptom data is impractical because of the general lack of predictability as to the time of occurrence of the episode. In such situations, therefore, it is known to employ a portable ECG recorder that allows the patient to be ambulatory during the measurement period. Such portable ECG equipment employs a magnetic tape to capture data during a period as long as 24 hours.

With advances in computer electronics, the so-called "memory loop recorder" has been developed. The memory loop recorder samples and digitizes the ECG signal which may then be stored as numeric values in a computer memory. Such computer memories typically have a capacity less than that obtainable by use of magnetic tape storage, however, the computer memory may be readily operated to store the ECG signal in a loop fashion over an indefinite period of time. For example, at any given time the memory loop recorder might store the last twenty minutes of ECG data. Newly arriving data continues to replace the oldest data in the memory.

The patient is provided with a control that is to be activated when an episodic abnormality is detected. At this time the recording continues for a predetermined time and then stops so that the memory holds both pre- and post-symptom data.

As any episodic cardiac abnormality may prove to be life-threatening, it is desirable to have the recorded ECG data reviewed by an electrocardiographer as soon as possible. In this regard, it is known to employ telephone line for the transmission of recorded ECG data to a remote display device where it can be reviewed and analyzed. In such systems, the stored ECG data is played back over the telephone line from beginning to end so that the electrocardiographer can view the progression of the abnormal episode.

The maximum loop length for each episode may be up to twenty minutes long and, therefore, the electrocardiographer may have to wait a significant period of time to see the data immediately preceding the abnormality. This delay may be critical in some cases and may delay the dispatch of emergency personnel. Any reduction in the length of the loop risks the loss of critical diagnostic data and requires the patient to rapidly recognize and respond to the onset of the abnormality.

SUMMARY OF THE INVENTION

The present invention provides a memory loop recorder which reduces delay in transmitting critical ECG data to a remote computer terminal. The delay is reduced by transmitting the ECG data in reverse time-order with the last acquired ECG data transmitted first.

Specifically, the present invention employs an electrode or the like for receiving electrocardiographic data. The data is communicated to a digitizer which samples and digitizes the electrocardiographic signal to produce a set of time-ordered digital words indicating the amplitude of the electrocardiographic signal at a plurality of instants in time. A memory communicating with the digitizer receives and stores these digital words in the order of their sampling times.

An episode marker, typically a button actuated by the patient, identifies one of the samples as a transmission starting point, and a transmission means, communicating with the storage means, reads the digital words in sequence from the transmission starting point in a reverse time-order for transmission to the remote display terminal.

It is thus one object of the invention to provide a transmission scheme which transmits diagnostically significant ECG information first, thus eliminating unnecessary delay. The transmission starting point may be designated to be immediately upon activation of the episode marker by the patient. In this case, the data covering the episode is transmitted first followed by the diagnostically important pre-symptom data. Later, the post-symptom data is also transmitted for a complete record of pre- and post-symptom data.

In one embodiment, the transmitter also communicates time-ordered ECG data in real time together with the reverse time-ordered ECG data from the memory. The remote display terminal receives the transmitted real time data and the recorded data and displays the real time and recorded data as data points in a graphical form along a first and second parallel abscissa indicating time. The real time data points are written to the display in a first direction along the first abscissa and the recorded data points are written to the display in a second direction opposite to the first direction along the second abscissa.

It is therefore another object of the invention displaying both real time and reverse time-ordered data, simultaneously, in a way that will be comprehensible to a human operator. By scrolling the time-ordered and time reversed data in opposite directions, at any given instant in time, the abscissa of both graphical representations will indicate an increasing time in the same direction and new data will be instantaneously viewable.

Other objects and advantages besides those discussed above shall be apparent to those experienced in the art from the description of the preferred embodiment of the invention which follows. In the description, reference is made to the accompanying drawings, which form a part hereof, and which illustrate one example of the invention. Such example, however, is not exhaustive of the various alternative forms of the invention, and therefore reference is made to the claims which follow the description for determining the scope of the invention.

DETAILED DESCRIPTION OF THE PREFERRED EMBODIMENT

Construction of the Invention

Figure 1:
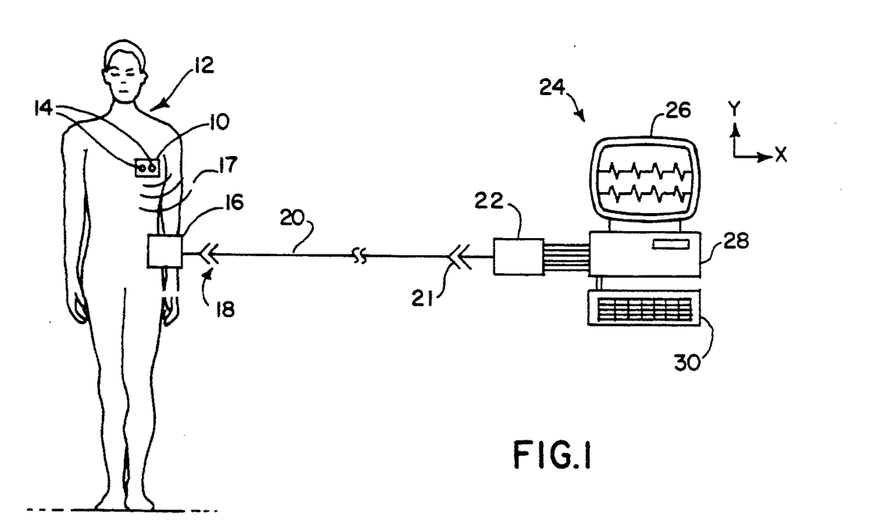
FIG. 1 shows a pictorial representation of the principal components of the present invention including the electrodes, the recording unit and the remote display terminal.

Referring to FIG. 1, an electrode assembly 10, attached to a patient 12, includes multiple electrodes 14 positioned to receive to two channels of electrocardiographic data as is generally understood in the art. A lightweight recording unit 16 is carried by the patient 12 on a harness (not shown) and positioned in proximity with the electrode assembly 10 to receive the electrocardiographic data from the electrodes 14.

In the preferred embodiment the electrode assembly 10 communicates the electrocardiographic data to the recording unit 16 by low powered radio waves. Wireless transmission of ECG data is well known in the art and wireless electrode assemblies 10 suitable for use with the present invention are commercially available from Transkinetics located in Canton, Massachusetts. A wireless electrode assembly 10 provides the patient 12 with improved mobility; however, alternatively the electrode assembly 10 may be connected to the recording unit 16 with conventional flexible wire leads.

The recording unit 16 may be connected to voice grade telephone line 20 by jack 18 for transmitting or receiving data. Principally, the telephone line 20 carries electrocardiographic data from the recording unit 16 to a remote display terminal 24 where it is received by interface unit 22 connected to the telephone line 20 by jack 21. The remote display terminal includes a display 26, a computer 28 and a keyboard 30 and may be a "personal computer" such as is well known in the art and commercially available through a variety of vendors.

The interface unit 22 also transmits data from the remote display terminal 24 and communicates that data via telephone line 20 to the recording unit 16. Such data is used to configure the recording unit 16 as will be described below and provides for control of data transfer from the recording unit 16 by an operator at the remote display terminal 24.

Figure 2:
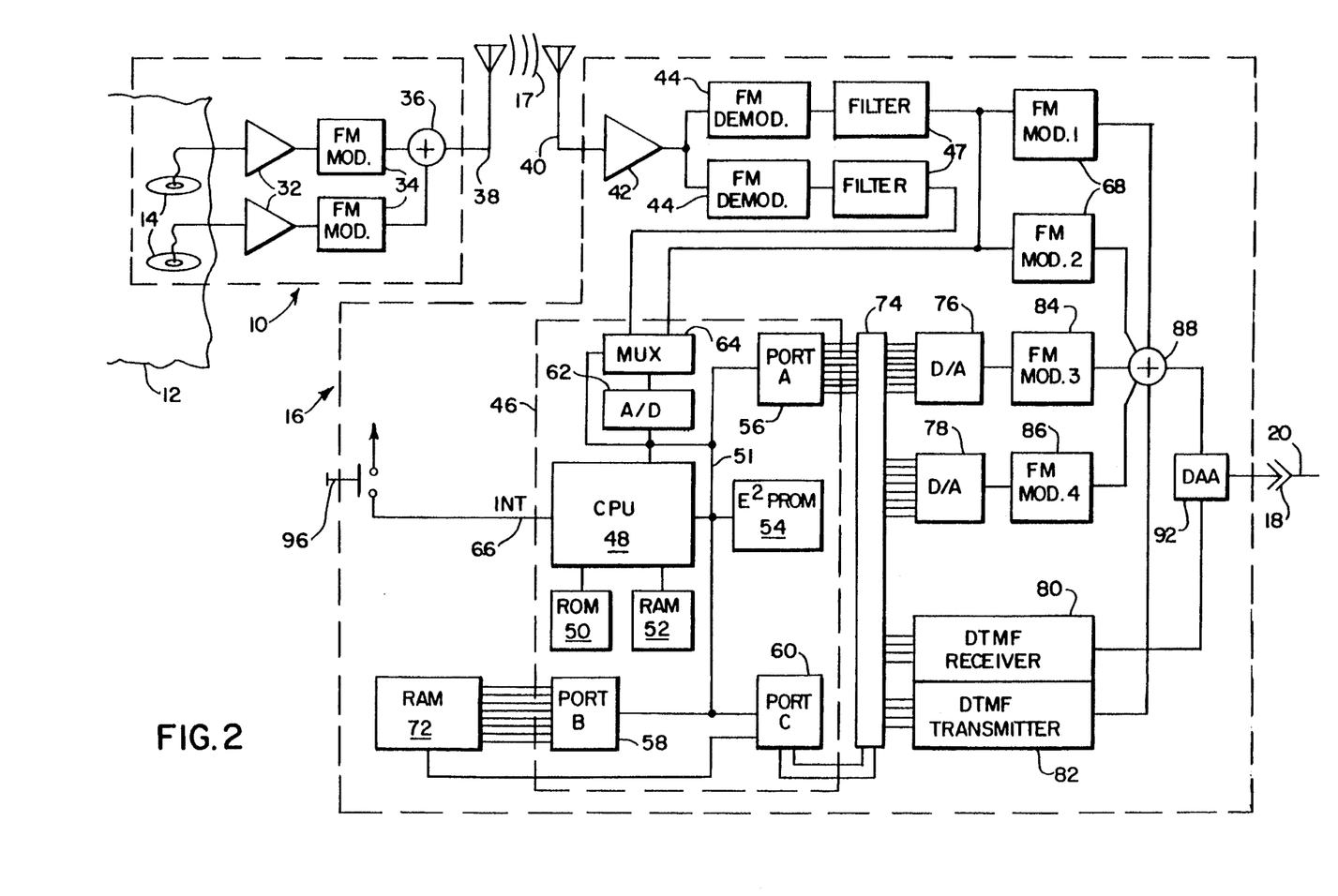
FIG. 2 is a block diagram of the recording unit and electrodes of FIG. 1.

Referring now to FIG. 2, two active electrodes 14 of the electrode assembly 10 are connected to the inputs of corresponding preamplifiers 32 to be measured against signals from reference electrodes (not shown) to develop two channels of ECG data. Each channel of ECG data, as amplified by preamplifiers 32 is input to a separate FM modulator 34 which FM modulates the ECG data at a separate carrier frequency. The outputs from the FM modulators 34 are summed at summing node 36 and transmitted as radio waves 17 via antenna 38.

The FM modulated radio waves 17 are received by antenna 40 on the recording unit 16. The signal received by the antenna 40 is amplified by amplifier 42 and then demodulated by two parallel connected FM demodulators 44 tuned to the separate carriers of the FM modulators 34 so as to reconstruct the two channels of ECG data.

These two channels of ECG data are each band limited by filters 47 to reduce their noise content and to prevent aliasing during the sampling and digitization of the ECG signals to follow.

The recording unit 16 incorporates a one chip microprocessor 46 having a CPU 48 connected by an internal bus 51 to an internal read only memory ("ROM") 50, a random access memory 52 ("RAM"), an electrically erasable programmable read only memory 54 ("EEPROM"), and three eight-bit ports: port A 56, port B 58 and port C 60. The internal bus 51 also connects the CPU 48 to an eight-bit internal A to D converter 62 which receives inputs from an analog multiplexer 64 also under the control of the CPU 48.

An external interrupt input 66, as will be understood to those of ordinary skill in the art, connects to the CPU 48 to allow the CPU 48 to respond to that input on a real time basis.

Such microprocessors are well known in the art and may be obtained commercially from Motorola Semiconductors Products Inc. of Austin, Texas, a subsidiary of Motorola Inc.

The two channels of filtered ECG data from the filters 47 are received by the inputs of the multiplexer 64, which, under the control of the CPU 48, samples the two channels of ECG data alternately, in rapid succession, to be digitized by the A to D converter 62. The digitized ECG data is then transmitted by the internal bus 51 to port B 58 to be stored in external RAM 72 comprising 512,000 eight-bit bytes. The reading and writing of the RAM 72 is controlled by the CPU 48 via lines from port C 60 which enables the RAM 72 and control the timing of the read and write cycles as is well understood in the art.

The sampling and digitizing of the two channels of ECG data by the multiplexer 64 and the A to D converter 62 occurs at 128 times per second for each channel resulting in 256 samples per second. Thus the RAM 72 can hold approximately twenty minutes of data from the two channels.

Port C 60, in addition to controlling RAM 72, also provides control lines for controlling multiplexer 74 which connect the eight-bits of port A alternatively to the inputs of one of: D to A converter 76, D to A converter 78 or the first four bits of dual tone multi-frequency ("DTMF") receiver 80 or to DTMF transmitter 82. In the latter case, port A serves as an input whereas in all the former cases, port A serves as an output.

D to A converters 76 and 78 are conventional eight-bit D to A converters as are known in the art and are commercially available from Motorola Semiconductors of Austin, Texas. The DTMF transmitter and receiver 82 and 80 synthesize and demodulate the frequency pairs required for the Touch Toner Telephone Dialing System employing combinations of one of four high and low frequency ranges to convey sixteen states over audio telephone line. The DTMF receiver and transmitter 80 and 82 may be purchased from a variety of vendors such as Motorola Semiconductors of Austin, Texas.

The D to A converters 76 and 78 provide outputs to audio FM modulators 84 and 86 which filter and modulate the data received from port A 56 with different audio carriers for transmission of the data on the telephone line 20.

The two channels of filtered ECG data from filters 47 are also connected to two FM modulators 68 having different audio carrier frequencies from the FM modulators 84 and 86 frequencies to provide real time transmission of the channel signals also via telephone line 20 without interfering with the signals from FM modulators 84 and 86.

The outputs of each of the FM modulators 84 and 86 and 68 are summed together with the output of the DTMF transmitter 82 by summing node 88 and connected to the analog input of the data-access-arrangement ("DAA") 92. The analog output of the DAA 92 is connected to DTMF receiver 80. The DAA 92 utilizes a four wire to two wire converter to provide full-duplex communication of data between the summing node 88, DTMF 80, and the telephone line 20, as is well understood in the art. DAA's may be readily purchased from a variety of vendors such as Rockwell International of Newport Beach, California.

Accordingly, the recording unit 16 may receive two channels of ECG data from the electrode assembly 10 and transmit that ECG data over the telephone line 20 through FM modulators 68 together with ECG data stored in RAM 72 and output through port A 56 D to A converters 76 and 78 and FM modulators 84 and 86. Alternatively, DTMF data may be transmitted or received over the telephone line 20.

The interrupt input to the CPU 48 connects to a push button 96 which may be activated by the patient 12, as will be described, to control the timing of the storage of ECG data from electrodes 14 into RAM 72.

Figure 3:
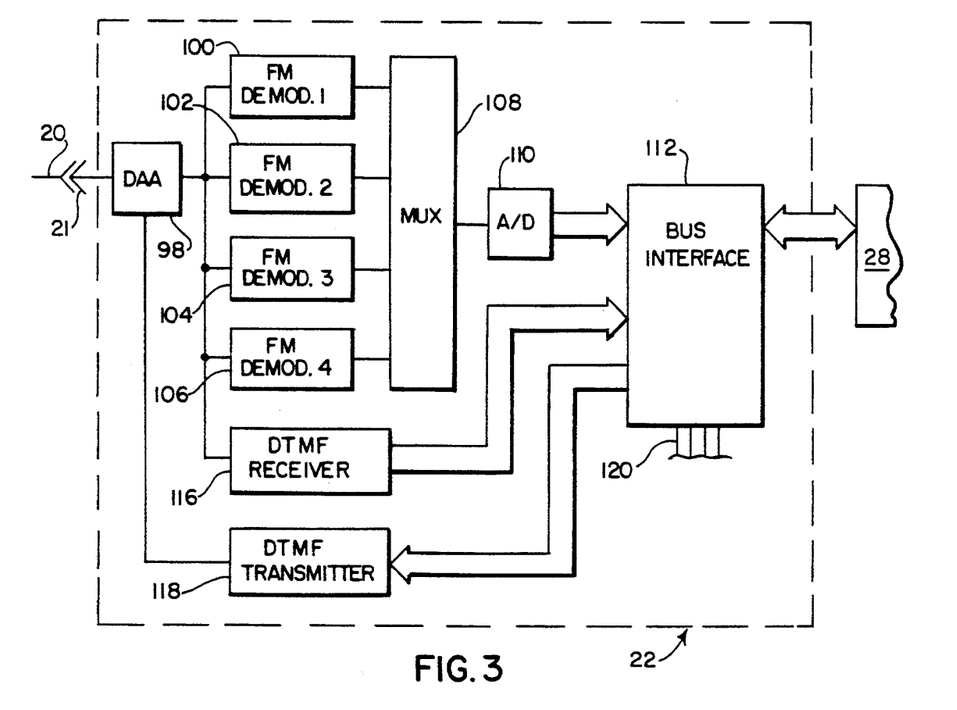
FIG. 3 is a block diagram of an interface portion of the remote display terminal of FIG. 1.

Referring now to FIGS. 1 and 3, the recording unit 16 communicates over telephone line 20 with the interface unit 22 which forms part of display terminal 24; the interface unit 22 receives information transmitted from the recording unit 16 via the telephone line 20 and may transmit information to the recording unit 16 via the telephone line 20. The telephone line 20 is connected through jack 21 to data access arrangement 98. The DAA 98 uses a two wire to four wire converter that channels the in-coming data from the telephone line 20 to a bank of four parallel connected FM demodulators 100, 102, 104, and 106 and to the DTMF receiver 116. The FM demodulators 100 through 106 demodulate the FM modulated ECG signals produced by the FM modulators 68, 84 and 86 of the recording unit 16 shown in FIG. 2. Thus, they are tuned for the particular audio carrier frequencies used in the FM modulators 68, 84 and 86. The output from the demodulators 100 through 106 is the filtered analog ECG signals.

The outputs of the FM demodulators 100 through 106 is connected to the inputs of multiplexer 108 which is also under control of computer 28. Multiplexer 108 selects the output of one FM demodulator 100 through 106 at a given time and directs that output to the input of A to D converter 110. A to D converter 110 digitizes the selected output and presents the digitized output to an input of bus interface 112.

The DAA 98 also connects the analog output of the DTMF transmitter to the telephone line 20 through jack 21. The four bit output of DTMF receiver 116 and the four-bit input of the DTMF transmitter are also connected to the bus interface 112.

Bus interface 112 communicates with the bus system of computer 28 and generally creates a virtual memory address for each of the FM demodulators 100-106 and the DTMF receiver and transmitter 116 and 118 which may be written to or read from by computer 28 so as to communicate digital data between computer 28 and the various components of the interface unit. Such interfacing techniques, described generally as memory mapped I/O, require coordination with the internal timing signals of the bus of the computer 28 and are well known in the art.

The bus interface 112 provides additional control outputs (not shown) to the multiplexer 108 to control the position of the multiplexer 108. Thus computer 28 may flexibly receive data transmitted from the recording unit 16 via telephone line 20, by FM modulation or by dual tone multi-frequency modulation, and transmit data to the recording unit 16 via dual tone multi-frequency modulation.

Figure 4:
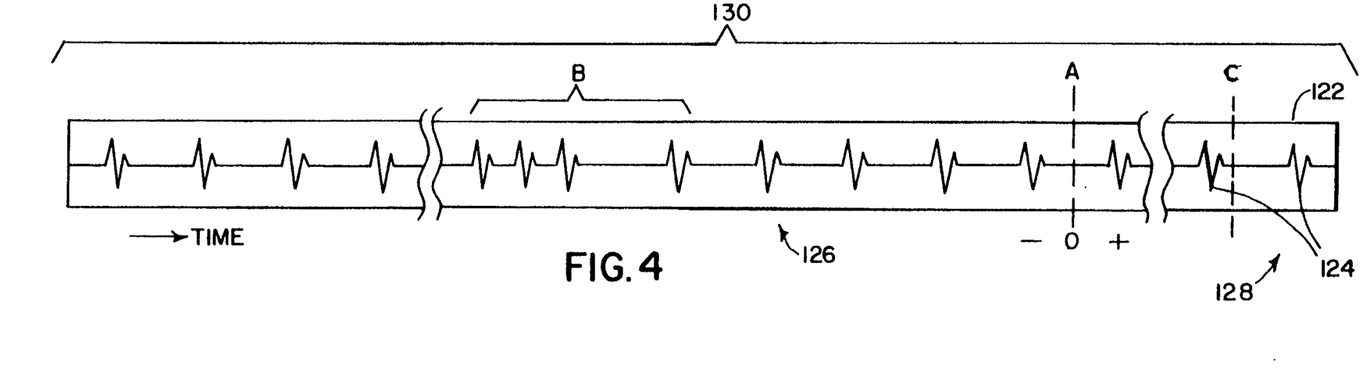
FIG. 4 is a schematic representation of a ECG signal as stored by the present invention showing an arrhythmic episode.

Referring now to FIG. 4, ECG data 122 as might be recorded by recording unit 16 includes a plurality of QRS complexes 124 indicating the contraction of a human heart. Typically such QRS complexes 124 are regularly spaced but under certain conditions they may exhibit arrhythmic behavior indicated generally by area B.

Such arrhythmias B may be recognized by the patient 12 at instant A at which time button 96 (shown in FIG. 2) is pressed by the patient 12. ECG data 122 occurring prior to instant A is termed pre-symptom 126 and data occurring after instant A is termed post-symptom data 128.

The recording unit 16 may be programmed to store a predetermined amount of pre-symptom and post-symptom data 126 and 128 which together determine a loop length 130.

OPERATION OF THE INVENTION

A. Initialization of the Loop Parameters

Referring again to FIG. 2, during operation of the present invention, the recording unit 16 receives two channels of ECG data from the electrode assembly 10 and stores that ECG data in one or more memory loops held in RAM 72. The storage of ECG data and the other functions of the recording unit 16 are controlled by the CPU 48 under the control of firmware in ROM 50.

The number, size and other parameters of the loop are stored in EEPROM 54 to be protected from erasure if the power is removed from the recording unit 16 and CPU 48 such as may occur during replacement of the recording unit's batteries.

The external controls required on the recording unit 16 have been minimized and include only push button 96. Therefore, the necessary loop parameter data held in EEPROM 54 are entered via the keyboard 30 of computer 28 and transmitted via telephone line 20 to the recording unit 16. It will be recognized that this approach beyond simplifying the operation of the recording unit by the patient 12, reduces the cost of the system by transferring the complexity of the programming interface to the single remote display terminal 24 and away from the multiple recording units 16 typically used with each such remote display terminal 24.

Figure 6:
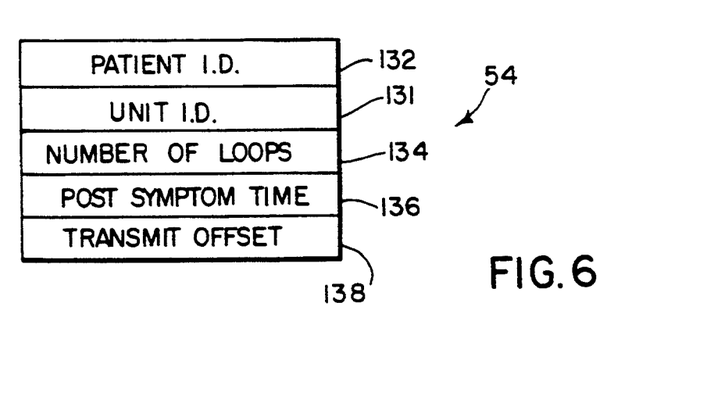
FIG. 6 is a schematic representation of a data structure stored in the recording unit of FIG. 2 for configuring the present invention via the remote display terminal.

Configuration of the recording unit 16 by the remote display terminal 24 must be performed prior to the recording unit's use. The CPU 48 of the recording unit 16 periodically monitors DTMF receiver 80 for transmission from the remote display terminal 24. When such transmissions are received, the CPU 48 suspends its other operations to accept the loop parameter data. Referring to FIG. 6, such loop parameter data includes generally a patient identification number 132, the recording unit 16 identification number 131, the number of loops 134 into which the RAM 72 will be divided for recording ECG data, the post-symptom time 136, and the transmit offset 138 which indicates a number of seconds before or after instant A (as shown in FIG. 4) that transmission of the ECG data will begin. By convention transmit offset values towards post-symptom data 128 are positive values whereas transmit offset values toward pre-symptom data 126 are negative values. The choices for each of these parameter data are dependant on one another and are provided in the following table I.

| Loop Numbers | Length in Minutes | Post-symptom Time |
| --- | --- | --- |
| 8 | 2.5 | .5 |
|   |   | 1 |
| 4 | 5 | 1 |
|   |   | 2.5 |
| 2 | 10 | 2.5 |
|   |   | 5 |
| 1 | 20 | 5 |
|   |   | 10 |

Figure 7:
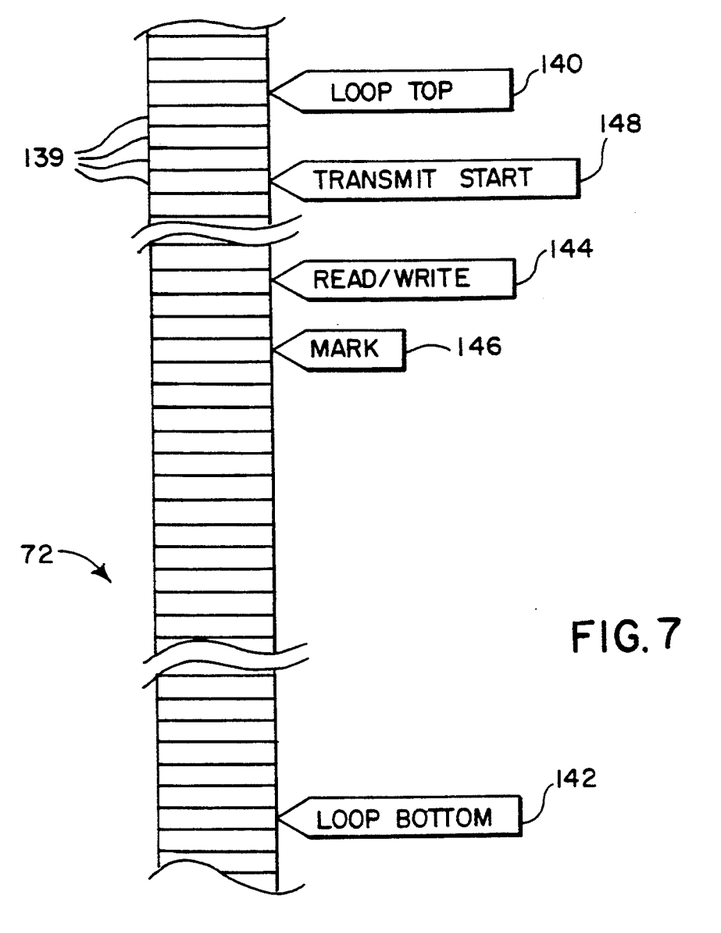
FIG. 7 is a schematic representation of the memory loop of the recording unit of FIG. 1 showing pointers designated by the data of the structure of FIG. 6.

Referring now to FIGS. 4, 6 and 7, once the loop parameter data has been entered into EEPROM 54, the CPU 48 calculates the necessary partitions in RAM 72 to create sufficient room for the various loops. The partition for each loop is indicated by two pointers to addresses 139 in RAM 72 indicating a loop top address 140 and loop bottom address 142. Loop bottom address 142 and loop top address 140 are separated by a value equal to twice the loop length in seconds times the sampling rate, in this case 128 samples per second.

B. Recording ECG Data

Once the recording unit is programmed, it begins accepting ECG data from the electrode assembly 10. At each of the addresses 139 of RAM 72 between the loop top address 140 and loop bottom address 142 an ECG signal sample is stored starting at the loop bottom 142 and progressing in sequence to the loop top 140. A read/write pointer 144 is incremented twice after the storage of each ECG sample (for each of the two channels of ECG data) to track the address at which the next sample should be stored. When the read/write pointer 144 equals the loop top address 140, the read/write pointer is set equal to the loop bottom address 142 and new ECG signals are stored over the old ECG samples. This process repeats indefinitely to provide a constant window of stored ECG data equal to the loop length.

When the patient 12 detects an abnormal episode, B, (shown in FIG. 4) the button 96 (shown in FIG. 2) is pressed activating an interrupt routine stored in ROM 50 which stores the value of the current read/write pointer 144 at a mark variable 146, which indicates the address of the ECG sample received at the instant A of FIG. 4. The read/write pointer 144 is now allowed to advance only a predetermined number of additional addresses for the acquisition of new ECG data determined by the post-symptom time 136 in EEPROM 54. The number of addresses by which the read/write pointer may advance after the identification of the mark variable 146 is calculated from the sample rate and the post-symptom time 136 programmed into EEPROM 54.

When the read/write pointer has advanced by the number of addresses indicated by the post-symptom time 136, writing in the loop defined by the loop top address 140 and the loop bottom address 142 stops and the read/write pointer advances a new loop if more than one loop is indicated in loops variable 134 in EEPROM 54. This process may then be repeated for the remaining loops with separate mark variables 146 being identified for each such loop. Thus multiple episodes B may be recorded if multiple loops are provided.

C. Transmitting ECG Data

Depending upon the severity of the episode B and the instructions by the doctor to the patient 12, the patient 12 may immediately transmit the stored ECG data in RAM 72 via telephone line 20 to the remote display terminal 24. In order to eliminate external controls on the recording unit 16 other than the event marker button 96, the ECG data transfer is initiated by the remote display terminal 24.

To initiate ECG data transfer from the recording unit 16 to the remote display terminal 24, the patient 12 contacts an operator at the remote display terminal 24 by means of a telephone handset and then connects jack 18 of the recording unit 16 to the telephone line 20 via a standard modular telephone jack. The CPU 48 normally, as mentioned before, monitors the jack 18 for receipt of DTMF data.

Upon detection of DTMF data requesting transmission of ECG data, the CPU 48 prepares to transmit the ECG data stored in the RAM 72. The first step in this transmission process requires the CPU 48 to transmit the number of loops data 134 stored in EEPROM 54 and of that number, the number of loops having recorded data in them. This information is transmitted via DTMF transmitter 82. The operator of the remote display terminal 24 then selects a loop for transmission, typically the last loop to be recorded with ECG data prior to the patient's telephone call, and communicates that decision to the CPU 48.

The CPU 48 then identifies a transmit start address 148 within the given loop. Generally, the transmit start address 148 will be the mark address 146 plus the transmit offset 138 if that sum is not greater than the loop top address 140. Otherwise, the transmit start address 148 will be the loop bottom address 142 plus the transmit offset 138 minus the difference between the loop top address 140 and the mark variable 146.

The ECG data from RAM 72 is transmitted in reverse time-order which means that successive ECG data from RAM 72 are read at the point indicated by the read/write pointer 144 with the read/write pointer 144 decremented after each such reading and the transmission of the read ECG data. The read/write pointer 144 begins at the address indicated by the transmission starting point 148 then proceeds to lower addresses until it reaches loop bottom address 142 at which time it is set equal to the loop top address 140 and continues to decrement until it again reaches the transmission starting point 148.

At the completion of the transmission of a given loop of ECG data in RAM 72, the operator of the remote display terminal 24 may request transmission of the other recorded loops. During this period of transmission of the ECG data stored in the loops of RAM 72, real time ECG data from FM modulator 68 may also be transmitted.

Referring to FIG. 3, at the interface unit, the current ECG data and the channels of recorded ECG data are read rapidly in sequence via the switching of multiplexer 108 by A to D converter 110 to provide a stream of digital data through bus interface 112 to the computer 28. The computer 28 may then display selected data on the display 26 by selectively setting pixels on the display 26 so as to create a rolling graphical representation of the received data.

D. Display of ECG data

Figure 5:
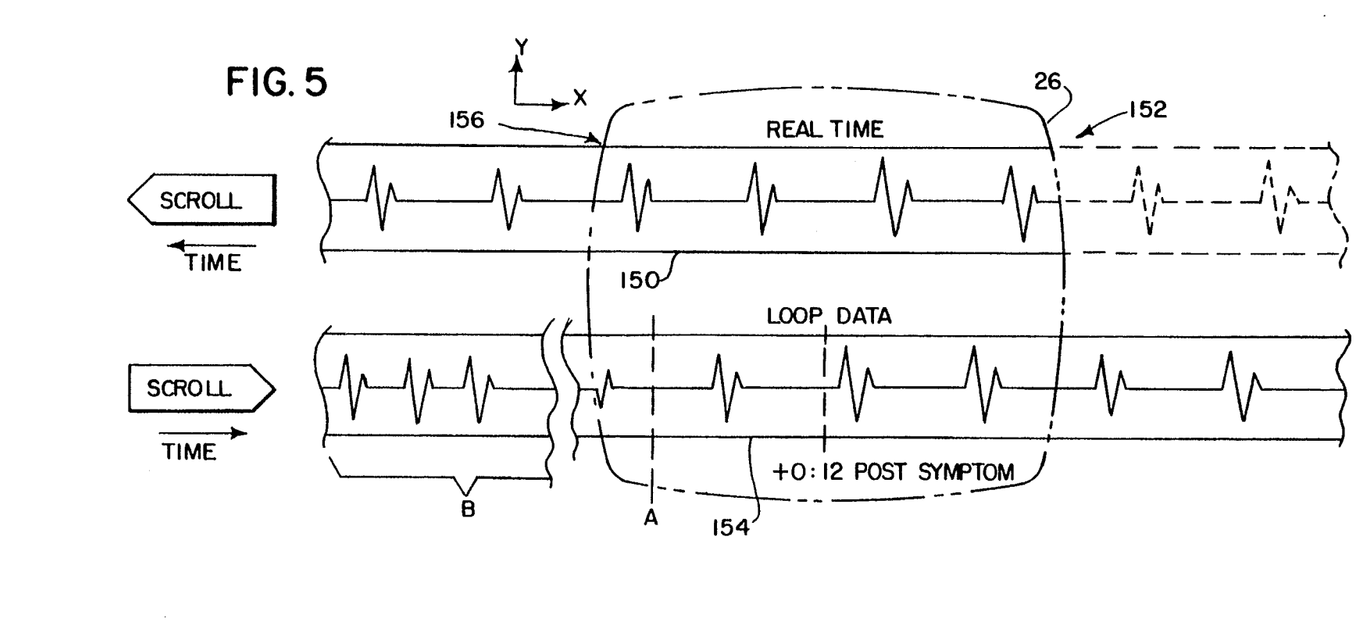
FIG. 5 is a schematic representation of the display of real time and stored ECG data on the remote display terminal employing countervailing scrolling to preserve a uniform time axis.

Referring now to FIG. 5, the remote display terminal 24 may display one or more channels of ECG data as transmitted by FM modulators 68 of the recording unit 16 and one or more channels of the loop data from RAM 72. The ECG data is plotted as a series of picture elements ("pixels") against a horizontal axis of time and a vertical axis of amplitude. The real time data from FM modulators 68 is displayed starting at the leftmost edge of the display 26 and using the value of the transmitted ECG data as a y-axis offset of a pixel location from a horizontal baseline 151. Successive pixels are then plotted at increasing x-axis locations on the display 26 moving the pixel x-axis location successively to the right on the display 26 until the rightmost edge 152 of the active area of the display 26 is reached. At this point, the previously plotted pixels may be erased and the process may begin again at the leftmost edge 156 of the display 26, or preferably the plotted pixels are "scrolled" to the left with new pixels being plotted at the rightmost edge 152 of the display 26. This scrolling is performed by rewriting each of the pixels plotted so far shifted in x-axis value by −1 to create room for the plotting of new pixels at the rightmost edge 152 of the display 26. The general effect is that the ECG graph appears to move to the left as new ECG data is received with the axis of increasing time being from left to right according to convention.

The recorded ECG data transmitted via FM modulators 84 and 86 is dealt with differently because the recorded ECG data is being transmitted in reverse time-order. The recorded ECG data is plotted first at the rightmost edge 152 of the display 26 with the value of the ECG data forming a Y offset from a horizontal baseline 154 selected so that the graphs of real time and recorded ECG data do not overlap. For new recorded ECG data, the x-axis value of the plotted pixel is decremented so that the plot proceeds from right to left preserving the convention of increasing time from left to right. When the leftmost edge 156 of the display 26 is reached, the plotted pixels may be erased and the plotting begun again at the rightmost edge 152 of the display 26 or preferably the display is scrolled to the right by rewriting the pixels so far plotted with their x-axis values incremented by 1 to create room at the leftmost edge 156 of the display 26 for plotting of new pixel data.

Thus, both the real time and the recorded ECG data as plotted observe normal left to right increasing time values for clear interpretation by an electrocardiographer. The relative and absolute time values of the abscissas of the plotted real time and recorded ECG data will constantly change. The rightmost edge 152 of the real time data will always be the ECG data taken at the current time. For the recorded ECG data, the time of the data at the center of the display 26 is calculated and displayed for the reference of the electrocardiographer.

Following the convention for the transmit offset value 138, post-symptom times are displayed with a plus sign and times in the pre-symptom times are displayed with a minus sign. This convention is reinforced by an alphanumeric label of "post-symptom" or "pre-symptom" appearing in the lower right corner of the display 26.

Thus, although the recorded ECG loop data is transmitted in reverse time-order, the display methodology provides for normal viewing of the recorded data with the advantage that the most relevant data is transmitted first to shorten the delay between recording and diagnosis.

Many modifications and variations of the preferred embodiment which will still be within the spirit and scope of the invention will be apparent to those with ordinary skill in the art. The number of channels that are recorded and displayed and the number and combinations of loops and loop lengths may be readily varied and may be increased with larger RAMs. In order to apprise the public of the various embodiments that fall within the scope of the invention, the following claims are made.

I claim:

1. An apparatus for monitoring and transmitting electrocardiographic data from a patient to a remote display terminal comprising:

an acquisition means for communication at least one electrocardiographic signal having a time-varying amplitude providing the electrocardiographic data from the patient to the apparatus;

a digitizing means communication with the acquisition means for receiving and sampling the electrocardiographic signal at a plurality of instants in time to produce samples and further digitizing the samples of the electrocardiographic signal to produce a set of time-ordered digital words indicating the amplitude of the electrocardiographic signal at the plurality of instants;

a storage means communicating with the digitizing means for receiving and storing the digital words according to their associated sampling instants in time;

an episode marker means, communicating with the storage means, for designating one instant as a transmit instant; and a transmission means communicating with the storage means for reading the digital words in sequence from the transmit instant in reverse time-order and transmitting the read digital words to the remote display terminal.

2. The apparatus as recited in claim 1 wherein the episode marker means, includes a patient accessible switch communicating with the storage means to be activated at a time during the storage of the digital words and the episode marker means designates as the transmit instant and instant associated with a digital word being stored at the time of activation of the switch.

3. The apparatus as recited in claim 1 wherein the episode marker means, includes a patient accessible switch communicating with the storage means to be activated at a time during the storage of the digital words and the episode marker means designates as the transmit instant an instant removed in time by a predetermined amount from the instant associated with a digital word being stored at the time of activation of the switch.

4. The apparatus recited in claim 1 wherein the storage means in partitioned into at least one event loop containing a predetermined number of addresses at which digital words may be stored and wherein the digital words are stored in sequence from a first address to a last address after which the stored digital words are replaced by new digital words stored in sequence from the first address to the last address.

5. The apparatus of claim 1 wherein the acquisition means ia radio transmitter and receiver pair for communication the electrocardiographic signal from the patient to the digitizing means.

6. The apparatus of claim 5 wherein the transmission means is a modulator means for modulating an audio carrier for transmission on a telephone line.

7. The apparatus of claim 1 wherein the acquisition means is a set of electrical conductors adapted to be attached between the patient and the digitizing means.

8. The apparatus of claim 1 wherein the transmission means is a modulator means for modulating an audio carrier for transmission on a telephone line.

9. The apparatus as recited in claim 1 wherein the transmission means transmits the digital words in sequence from the transmit instant in reverse time-order so that every word transmitted is transmitted in reverse time order.

10. An apparatus for monitoring and transmitting electrocardiographic data from a patient to a remote display terminal comprising:
- an acquisition means for communication at least one electrocardiographic signal having a time varying amplitude providing the electrocardiographic data from the patient to the apparatus;
- a digitizing means communication with the acquisition means for receiving and sampling the electrocardiographic signal at a plurality of instants in time to produce samples and further digitizing the samples of the electrocardiographic signal to produce a set of time-ordered digital words indicating the amplitude of the electrocardiographic signal at the plurality of instants;
- a storage means communication with the digitizing means for receiving and storing the digital words according to their associated sampling instants in time;
- an episode marker means, communicating with the storage means, for designating one instant as a transmit instant; and
- a transmission means communicating with the digitizing means and the storage means for transmitting to the display terminal the time-ordered digital words at the plurality of instants as real time data and for reading the digital words in sequence from the transmit instant in reverse time-order and also transmitting the read digital words as recorded data.

11. The apparatus of claim 10 wherein the acquisition means is a set of electrical conductors adapted to be attached between the patient and the digitizing means.

12. The apparatus of claim 10 wherein the acquisition means is a radio transmitter and receiver pair for communicating the electrocardiographic signal from the patient to the digitizing means.

13. A system for monitoring, transmitting, and displaying electrocardiographic data from a patient comprising:
- an acquisition means for communication at least one electrocardiographic signal having a time varying amplitude providing the electrocardiographic data from the patient to the apparatus;
- a digitizing means communication with the acquisition means for receiving and sampling the electrocardiographic signal at plurality of instants in time to produce samples and further digitizing the samples of the electrocardiographic signal to produce a set of time-ordered digital words indicating the amplitude of the electrocardiographic signal at the plurality of instants;
- a storage means communicating with the digitizing means for receiving and storing the digital words according to their associated sampling instants in time;
- an episode marker means, communicating with the storage means, for designating one instant as a transmit instant;
- a transmission means communicating with the digitizing means and the storage means for transmitting the time-ordered digital words in a transmission order at the plurality of instants as real time data, and for reading the digital words in sequence from the transmit instant, in reverse time-order and transmitting the read digital words as recorded data in a transmission order; and
- a remote display terminal for receiving the transmitted real time data and recorded data
  wherein the display terminal displays the real time data and recorded data as data points in graphical form with a first and second parallel abscissa indicating time and a first and second ordinate indicating the amplitude of the electrocardiographic data associated with the data points, for the real time data and recorded data respectively, and
  wherein the data points of real time data are written across the display in a first direction along the first abscissa with respect to their transmission order and wherein the data points of the recorded data are written across the display in a second direction opposite to the first direction along the second abscissa with respect to their transmission order.

14. A display apparatus for simultaneously displaying real time electrocardiographic data received in time-order and recorded electrocardiographic data received in reverse time-order, the display apparatus comprising:
- a computer/interface system including input interface circuitry means for receiving the real time electrocardiographic data and recorded electrocardiographic data according to a respective transmission order and output interface circuitry means for generating in response to a computer operating in accordance to a stored program, a plurality of data points for each datum having ordinate values related to the value of the datum, and abscissa values related to the relative instants of time associated with each datum so that the abscissa values for the data points of the real time data are proportional to their transmission order and wherein the abscissa values of the data points of the recorded data are proportional to the negative of their transmission order; and
- a user readable screen receiving the data points and displaying the data points at the abscissa and ordinate values.

15. An apparatus for monitoring, transmitting, and displaying electrocardiographic data from a patient comprising:

electrode means for receiving an electrocardiographic signal having a time varying amplitude providing the electrocardiographic data from the patient to the apparatus;

a memory means having addresses and communicating with the electrode means for receiving and storing the electrocardiographic data, wherein the memory means is partitioned into at least one event loop containing a predetermined number of addresses at which digital words may be stored and wherein the digital words are stored in sequence from a first address to a last address after which the stored digital words are replaced by new digital words stored in sequence from the first address to the last address;

a user activated switch means communicating with the memory means for designating one instant as a transmit instant wherein the transmit instant is an instant removed in time by a predetermined amount from the instant associated with a digital word being stored at the time of activation of the switch means;

a transmission means communicating with the memory means for reading the digital words in sequence from the transmit instant and transmitting the read digital words;

a remote terminal having a display means for receiving the read transmitted digital words and for displaying the read transmitted digital words and an inputting means for inputting input data and transmitting the input data to the apparatus; and a reception mans for receiving a value of at least one of the predetermined amount and the first and last address from the remote terminal.

* * * * *